United States Patent [19] [11] 4,133,817
Lourens et al. [45] Jan. 9, 1979

[54] 11-OXA-PROSTAGLANDIN ANALOGS

[75] Inventors: Gerhardus J. Lourens, Rand Park Ridge Extn 1; Johannes M. Koekemoer, Pretoria, both of South Africa

[73] Assignee: Chembro Holdings (Proprietary) Limited, Johannesburg, South Africa

[21] Appl. No.: 681,742

[22] Filed: Apr. 29, 1976

[30] Foreign Application Priority Data
Apr. 30, 1975 [ZA] South Africa .................. 75/2806

[51] Int. Cl.² .................. C07D 317/44; C07D 307/20
[52] U.S. Cl. .................. 260/340.9 P; 260/347.3; 260/347.4
[58] Field of Search ............ 260/347.3, 347.4, 340.9 P

[56] References Cited
PUBLICATIONS
Harrison et al., Tetrahedron Letters, No. 32, pp. 2733-2736, (1974).

Primary Examiner—Natalie Trousof
Assistant Examiner—Bernard Dentz
Attorney, Agent, or Firm—Cushman, Darby & Cushman

[57] ABSTRACT
The invention provides compounds of the formula 1 which are useful as hypertensive, anti-ulcer, anti-asthmatic and nasal decongestant agents and methods of preparing these compounds:

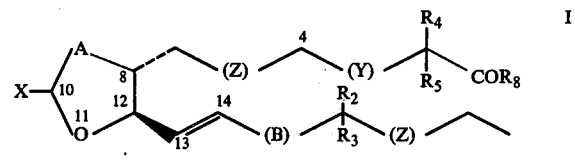

wherein
A represents —C=O or α—C ... OH
B represents

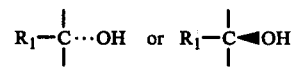

$R_1$ represents H, lower alkyl or substituted lower alkyl
Z represents $CH_2$—$CH_2$ or C=C in the cis configuration
$R_2$ and $R_3$, the same or different, represent H or substituted or unsubstituted lower alkyl;
Y is —S—, —O— or —$CR_6R_7$
$R_4$, $R_5$, $R_6$ and $R_7$, the same or different, represent H, substituted or unsubstituted lower alkyl or halogen
X is H or OH
$R_8$ is $OR_9$ or $NR_9R_9$
$R_9$ is H or an alkyl group, and when X is OH and A is α—C ... OH then together they may form the group

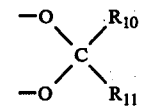

wherein $R_{10}$ and $R_{11}$, the same or different, are alkyl, hydrogen or a carbocyclic group of 4 to 6 carbon atoms.

10 Claims, 2 Drawing Figures

SCHEME (a)
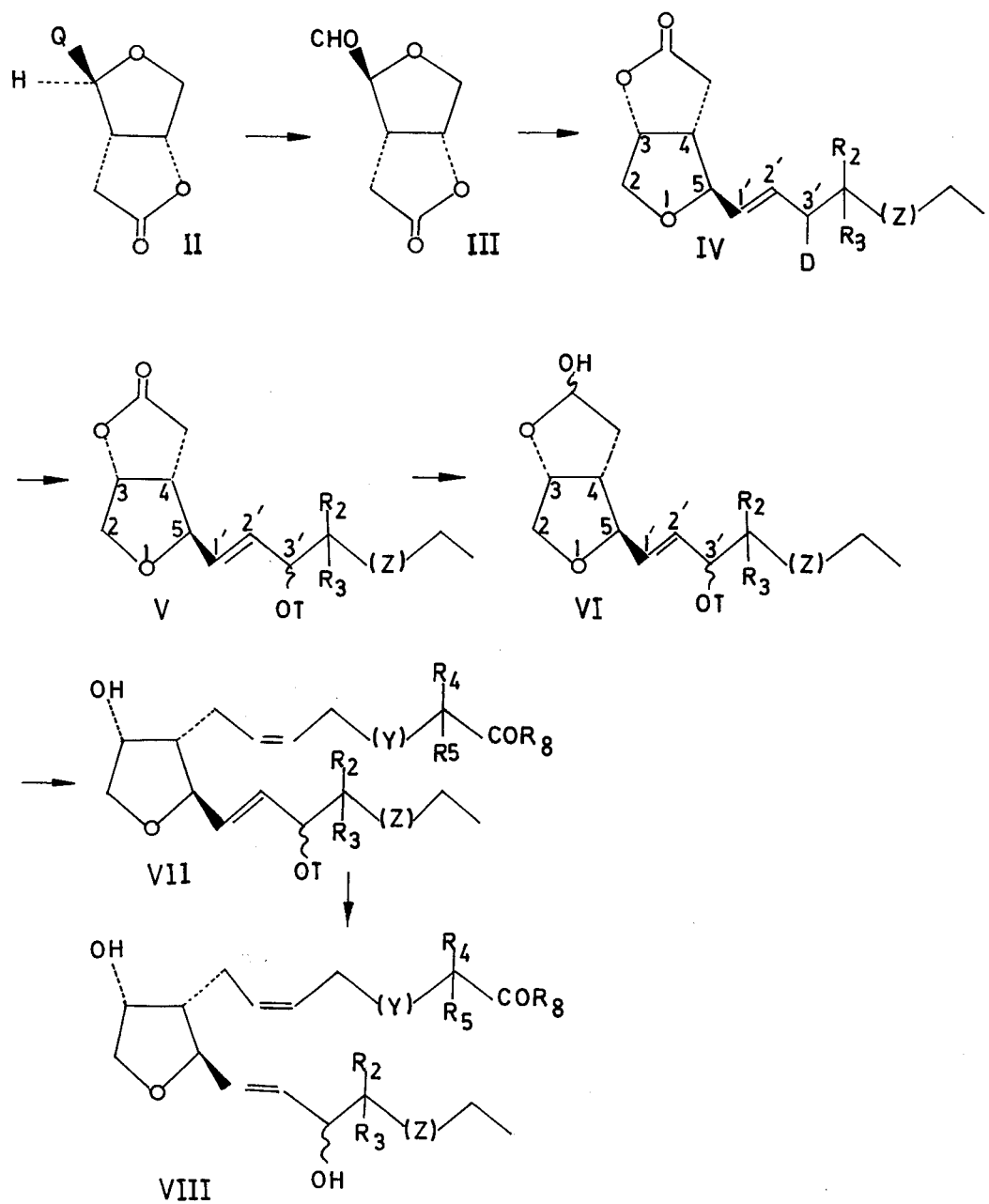

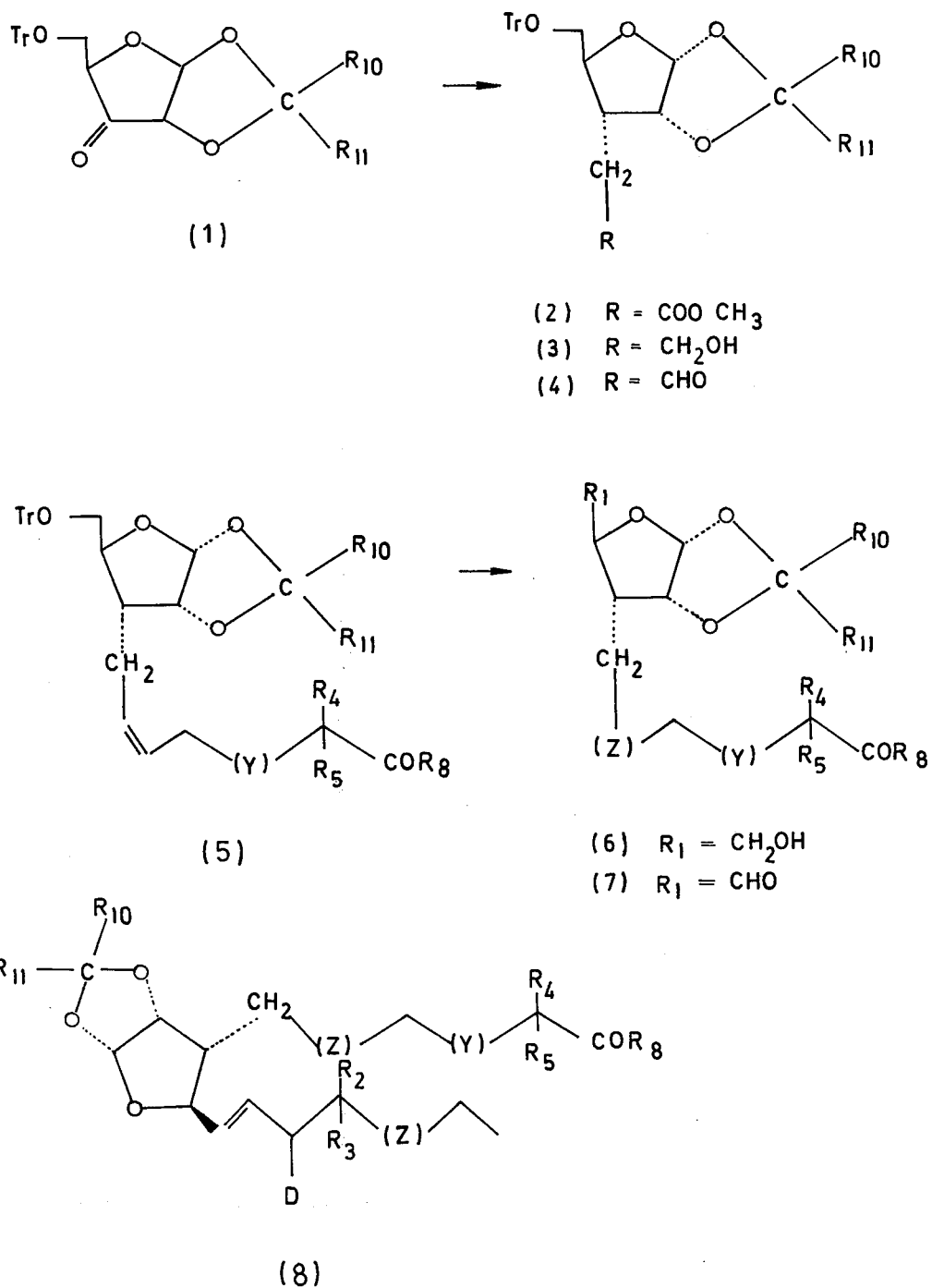

11-OXA-PROSTAGLANDIN ANALOGS

This invention relates to novel 11-oxa-prostaglandin analogues, derivatives thereof, and methods for their preparation.

The novel compounds of the invention are represented by the formula:

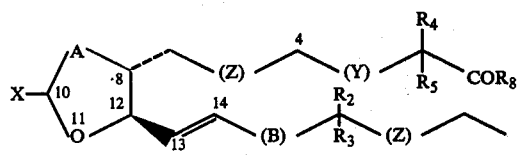

wherein
A represents —C=O or α—C ... OH
B represents

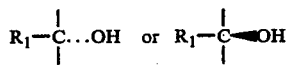

$R_1$ represents H, lower alkyl or substituted lower alkyl

Z represents $CH_2$—$CH_2$ or C=C in the cis configuration $R_2$ and $R_3$, the same or different, represent H or substituted or unsubstituted lower alkyl;

Y is —S—, —O— or —$CR_6R_7$ $R_4$, $R_5$, $R_6$ and $R_7$, the same or different, represent H, substituted or unsubstituted lower alkyl or halogen X is H or OH $R_8$ is $OR_9$ or $NR_9R_9$ $R_9$ is H or an alkyl group, and when X is OH and A is α—C ... OH then together they may form the group

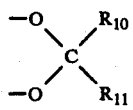

wherein $R_{10}$ and $R_{11}$, the same or different, are alkyl, preferably lower alkyl, hydrogen or a carbocyclic group of 4 to 6 carbon atoms.

Preferred compounds of the Formula I are those in which:
A is as defined above
B is $R_1$—C ... OH
$R_1$ is H or methyl
$R_2$ and $R_3$, the same or different, are H or methyl;
Y is as defined above
$R_4$, $R_5$, $R_6$ and $R_7$, the same or different, are H, lower alkyl or fluoro.
X is as defined above
$R_8$ is as defined above
$R_9$ is H or lower alkyl In the above formulae the term "lower alkyl" refers to alkyls of 1 to 4 carbon atoms such as methyl, ethyl and propyl. When the alkyls are substituted they may be substituted by halogen atoms such as fluorine. An example of a substituted alkyl is trifluoromethyl.

Particular examples of compounds of the invention are:

9α,15α-dihydroxy-11-oxa-prosta-cis-5:6-trans-13:14 dienoic acid
9α,15α-dihydroxy-15β-methyl-11-oxa-prosta-cis-5:6-trans-13:14-dienoic acid
9α,15α-dihydroxy-16,16-dimethyl-11-oxa-prosta-cis-5:6-trans-13:14-dienoic acid
9α,15α-dihydroxy-16-methyl-11-oxa-prosta-cis-5:6-trans-13:14-dienoic acid
9α,15α-dihydroxy-2,2-dimethyl-11-oxa-prosta-cis-5:6-trans-13:14-dienoic acid
2,2-difluoro-9α,15α-dihydroxy-11-oxa-prosta-cis-5:6-trans-13,14-dienoic acid
15α-hyroxy-11-oxa-9-oxo-prosta-cis-5:6-trans-13:14-dienoic acid methyl ester
9α,15α-dihydroxy-3,3-dimethyl-11-oxa-prosta-cis-5:6-trans-13:14-dienoic acid
3,3-difluoro-9α,15α-dihydroxy-11-oxa-prosta-cis-5:6-trans-13:14-dienoic acid
9α,15α-dihydroxy-3,11-di-oxa-prosta-cis-5:6-trans-13:14-dienoic acid
15α-hydroxy-15β-methyl-11-oxa-9-oxo-prosta-cis-5:6-trans-13:14-dienoic acid
15α-hydroxy-16,16-dimethyl-11-oxa-9-oxo-prosta-cis-5:6-trans-13:14-dienoic acid
15α-hydroxy-16-methyl-11-oxa-9-oxo-prosta-cis-5:6-trans-13:14-dienoic acid
2,2-dimethyl-15α-hydroxy-11-oxa-9-oxo-prosta-cis-5:6-trans-13:14-dienoic acid
2,2-difluoro-15α-hydroxy-11-oxa-9-oxo-prosta-cis-5:6-trans-13:14-dienoic acid
3,3-dimethyl-15α-hydroxy-11-oxa-9-oxo-prosta-cis-5:6-trans-13:14-dienoic acid
3,3-difluoro-15α-hydroxy-11-oxa-9-oxo-prosta-cis-5:5-trans-13:14-dienoic acid
3,11-di-oxa-15α-hydroxy-9-oxo-prosta-cis-5:6-trans-13:14-dienoic acid
9α,15α-dihydroxy-15β-methyl-11-oxa-prost-trans-13:14-enoic acid methyl ester
9α,15α-dihydroxy-16,16-dimethyl-11-oxa-prost-trans-13:14-enoic acid methyl ester
9α,15α-dihydroxy-16-methyl-11-oxa-prost-trans-13:14-enoic acid methyl ester
9α,15α-dihydroxy-2,2-dimethyl-11-oxa-prost-trans-13:14-enoic acid methyl ester
2,2-difluoro-9α,15α-dihydroxy-11-oxa-prost-trans-13:14-enoic acid methyl ester
9α,15α-dihydroxy-3,3-dimethyl-11-oxa-prost-trans-13:14-enoic acid methyl ester
3,3-difluoro-9α,15α-dihydroxy-11-oxa-prost-trans-13:14-enoic acid methyl ester
9α,15α-dihydroxy-3,11-di-oxa-prost-trans-13:14-enoic acid methyl ester
15α-hydroxy-15β-methyl-11-oxa-9-oxo-prost-trans-13:14-enoic acid methyl ester
16,16-dimethyl-15α-hydroxy-11-oxa-9-oxo-prost-trans-13:14-enoic acid methyl ester
15α-hydroxy-16-methyl-11-oxa-9-oxo-prost-trans-13:14-enoic acid methyl ester
15α-hydroxy-2,2-dimethyl-11-oxa-9-oxo-prost-trans-13:14-enoic acid methyl ester
2,2-difluoro-15α-hydroxy-11-oxa-9-oxo-prost-trans-13:14-enoic acid methyl ester
3,3-dimethyl-15α-hydroxy-11-oxa-9-oxo-prost-trans-13:14-enoic acid methyl ester
3,3-difluoro-15α-hydroxy-11-oxa-9-oxo-prost-trans-13:14-enoic acid methyl ester
3,11-di-oxa-15α-hydroxy-9-oxo-prost-trans-13:14-enoic acid methyl ester 9α,10α,15α-trihydroxy-11-oxa-9:10-isopropylidene-prost-trans-13:14-enoic acid methyl ester 9α,10α,15α-trihydroxy-15β-methyl-11-oxa-9:10-isopropylidene-prost-trans-13:14-enoic acid methyl ester 9α,10α,15α-trihydroxy-16,16-dimethyl-11-oxa-9:10-isopropylidene-prost-trans-13:14-enoic acid methyl ester 9α,10α,15α-trihydroxy-16-methyl-11-oxa-9:10-isopropylidene-prost-trans-13:14-enoic acid methyl ester 9α,10α,15α-trihydroxy-2,2-dimethyl-11-oxa-9:10-isopropylidene-prost-trans-13:14-enoic acid methyl ester 9α,10α,15α-trihydroxy-2,2-difluoro-11-oxa-9:10-isopropylidene-prost-trans-13:14-enoic acid methyl ester 9α,10α,15α-trihydroxy-3,3-dimethyl-11-oxa-9:10-isopropylidene-prost-trans-13:14-enoic acid methyl ester 9α,10α,15α-trihydroxy-3,3-difluoro-11-oxa-9:10-isopropylidene-prost-trans-13:14-enoic acid methyl ester 9α,10α,15α-trihydroxy-3,11-di-oxa-9:10-isopropylidene-prost-trans-13:14-enoic acid methyl ester 9α,10α,15α-trihydroxy-15β-methyl-11-oxa-9:10-isopropylidene-prosta-cis-5:6-trans-13:14-dienoic acid methyl ester 9α,10α,15α-trihydroxy-16,16-dimethyl-11-oxa-9:10-isopropylidene-prosta-cis-5:6-trans-13:14-dienoic acid methyl ester 9α,10α,15α-trihydroxy-16-methyl-11-oxa-9:10-isopropylidene-prosta-cis-5:6-trans-13:14-dienoic acid methyl ester 9α,10α,15α-trihydroxy-2,2-dimethyl-11-oxa-9:10-isopropylidene-prosta-cis-5:6-trans-13:14-dienoic acid methyl ester 9α,10α,15α-trihydroxy-2,2-difluoro-11-oxa-9:10-isopropylidene-prosta-cis-5:6-trans-13:14-dienoic acid methyl ester 9α,10α,15α-trihydroxy-3,3-dimethyl-11-oxa-9:10-isopropylidene-prosta-cis-5:6-trans-13:14-dienoic acid methyl ester 9α,10α,15α-trihydroxy-3,3-difluoro-11-oxa-9:10-isopropylidene-prosta-cis-5:6-trans-dienoic acid methyl ester 9α,10α,15α-trihydroxy-3,11-di-oxa-9:10-isopropylidene-prosta-cis-5:6-trans-13:14-dienoic acid methyl ester Although the invention includes within its scope racemic mixtures containing compounds of the Formula I, the invention provides, as a particularly preferred form, such compounds substantially free of other geometric and optically active isomers. In particular, it is preferred that the compounds are substantially free from their optically active enantiomorphs. "Substantially free" means that any contamination from the unwanted isomer is as low as possible, but at least less than 1% by weight.

The novel compounds of the invention have useful pharmaceutical properties and, in particular, act as inhibitors of acid production by gastric mucosa and as agents active in the constriction or dilation of smooth muscle. The compounds of the invention have hypertensive, anti-ulcer, anti-asthmatic and nasal decongestant activity.

The compounds of the invention may be administered in any suitable pharmaceutical form such as tablets, syrups, suspensions, nasal sprays, aerosols and injectable forms. The carriers, excipients, solvents and the like for these formulations can be any known in the art. The invention also includes within its scope a pharmaceutical composition containing as an active ingredient a compound of the Formula I.

The novel compounds of the invention may be produced from novel intermediates, which may be prepared by a stereospecific route. There follows a diagram showing a stereospecific route for preparing the novel intermediates of formula II. Referring to the diagram compounds of type (III) such as D-glucose or D-xylose, whose absolute stereochemical configuration is known, are converted by known methods into (IV) wherein Y represents a cyclic base stable group such as isopropylidene or cyclohexylidene. (IV) is oxidized to (V) for example using either ruthenium tetroxide (B. T. Lawton, W. A. Szarek, and J. K. N. Jones, Carbohydrate Research 10, 456–458, 1969) or dimethylsulphoxide and anhydride such as $P_2O_5$ (K. Onodera, S. Hirano and N. Kashimura, Carbohydrate Research 6, 176–285, 1968) or acetic anhydride (W. Sowa, Can. J. Chem., 46, 1586, 1968).

(V) is converted to (VI) wherein Z represents a hydrocarbyl group for example by a Wittig reaction (A. Rosenthal and L. Benzing Nguyen, J. Org. Chem. 34, 1029, 1969).

Compounds of type (VI) are converted to (X) by stereospecific reduction from the β-face, for example using a catalyst such as palladium on carbon (A. Rosenthal and L. Benzing Nguyen, J. Org. Chem. 34, 1029) or Raney-Nickel in an alcohol. If Q contains blocking groups $R_2$, $R_3$ and $R_4$ which are acid labile they are selectively removed and replaced by acid stable groups, for example, alkylidene to diacyl. (X) is converted to (XI) by removal of the blocking group Y with aqueous acid to give novel compounds of type (XI). (XI) is converted into (II) by reaction with a suitable haloacid in a solvent such as a dry acid or dry non-hydroxy solvent optionally containing an acid chloride or anhydride followed either by reduction of the halo substituted intermediate with a suitable catalyst, such as 10% palladium on carbon in the presence of hydrogen and a nitrogenous base, such as a trialkylamine, or reaction with the salt of an alkyl or aryl mercaptan to give the corresponding mercapto-intermediate followed by desulfurization, for example with Raney-Nickel. Alternatively, (XI) is converted into (II) by treatment with a suitable acid chloride or anhydride followed by reaction with a suitable haloacid in a dry non-hydroxylic solvent. The halo substituted intermediate is then treated in the manner described above to give (II).

Serial No. 681,742

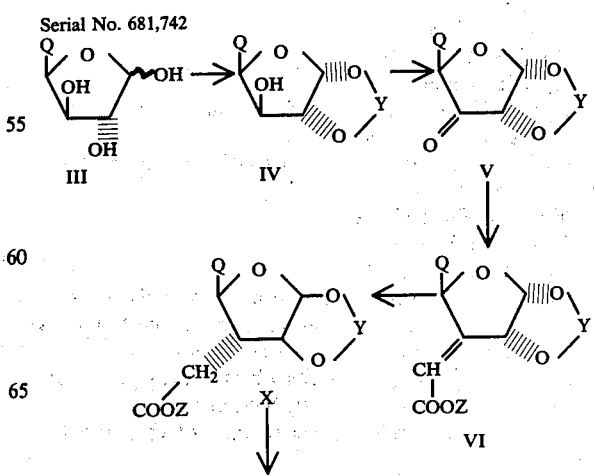

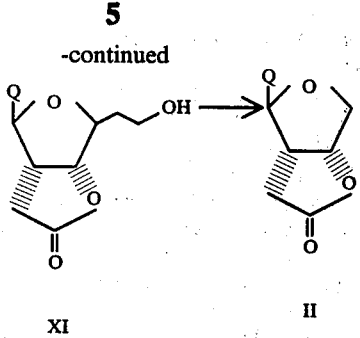

XI → II

The novel intermediates have the formula II

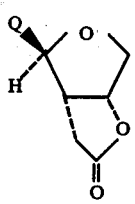

II wherein Q represents a hydrocarbyl group in which the α-carbon atom is activated by a suitable blocked or unblocked functional group rendering it susceptible to oxidation, preferably to an aldehyde.

Q preferably represents one of the groups:

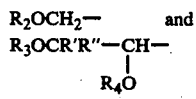

wherein $R_2$, $R_3$ and $R_4$, the same or different, each represents H or a suitable blocking group and $R_3$ and $R_4$ together may be $>C=O$; and $R'$ and $R''$, the same or different, each represents hydrogen or hydrocarbyl group which is optionally substituted.

Suitable blocking groups are known in the art and are preferably acyl or alkyl blocking groups. Suitable acyl blocking groups have the formula $R'''CO-$ wherein $R'''$ is an alkyl group, which preferably contains 1 to 4 carbon atoms or a phenyl group. The alkyl and phenyl groups may be substituted or unsubstituted. Examples of such blocking groups are acetyl and benzoyl. The alkyl blocking groups are preferably lower alkyl groups containing 1 to 4 carbon atoms which may be substituted. Examples of such blocking groups are trityl, benzyl and methyl.

The blocking groups are preferably acid stable.

The hydrocarbyl groups of $R'$ and $R''$ are preferably lower alkyl of 1 to 4 carbon atoms which may be substituted with groups such as hydroxy or hydroxy blocked by a blocking group as described above. It is preferred that both $R'$ and $R''$ are hydrogen.

One particular method of producing compounds of the formula I is illustrated diagrammatically in the attached Scheme (a):

(i) Compound II is oxidised to compound III. If it is necessary in the oxidation to cleave a carbon-carbon bond to which are attached hydroxy or blocked hydroxy groups, the oxidising agent may be sodium metaperiodate in a solvent such as ethanol or aqueous ethanol. If no such cleavage is required, the oxidising agent may be dimethylsulphoxidedicyclohexylcarbodiimide in the presence of a catalyst such as pyridinium trifluoro-acetate.

(ii) A first side chain is then coupled to the compound III by means of a modified Wittig reaction using an appropriate alkylated phosphonate. This reaction produces a trans double bond at the coupling point thereby producing the compound IV, wherein Z, $R_2$ and $R_3$ have the same meaning as in Formula I and D is $=O$,

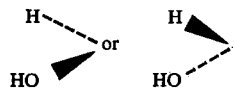

This coupling reaction is well known in the literature, an illustrative reference being: E. J. Corey, T. K. Schaaf, W. Huber, U. Koelliker and N. M. Weinschenker, J.Am.Chem.Soc., 92, 397 (1970); E. J. Corey et al, J.Am.Chem.Soc., 93, 1491 (1971).

(iii) If D of formula IV is $=O$ then the compound is reduced with a mild metal hydride reducing agent such as zinc borohydride or sodium borohydride. In the case of zinc borohydride the reaction is carried out in an inert solvent such as dimethoxyethane, tetrahydrofuran or ether, whereas in the case of sodium borohydride an inert or alcohol solvent may be used. The reduction must not be too severe otherwise the lactone will be reduced.

(iv) The hydroxy group of formula IV is then protected by means of a suitable base stable blocking group to give a compound V. Suitable base stable blocking groups are produced by reacting the hydroxy group with reagents such as dihydropyran or ethyl vinyl ether.

(v) The blocked compound V is reduced to produce compound VI wherein T is a base stable blocking group, and Z, $R_2$ and $R_3$ are as previously defined. The reduction involves the reduction of the lactone to a lactol using a metal hydride such as diisobutyl aluminium hydride. This reduction is well known in the art.

(vi) The second side chain is then coupled to the compound VI using a Wittig reaction in a polar solvent such as dimethylsulphoxide. This reaction is well known in the art, an illustrative reference being as in (ii). In compound VII, Z, Y and $R_4$, $R_5$ and $R_8$ have the same meaning as in Formula I. The 5,6 cis double bond may be selectively reduced using catalytic hydrogenation.

(vii) The blocking group is then removed by treatment with mild acid. Suitable acids are organic acids present in an amount of 60 to 90 v/v percent and mineral acids present in an amount of 5 to 10 v/v percent. Examples of organic acids are acetic acid, formic acid, oxalic acid and propionic acid and examples of mineral acids are sulphuric acid and hydrochloric acid.

The treatment with the acid is generally performed at a temperature of from 0° to 25° C.

(viii) If the resulting product is a racemic mixture, resolution of the isomers may take place using conventional methods, for example column chromatography on a suitable absorbent such as silica gel with an appropriate eluant such as mixtures of benzene and ethylacetate.

(ix) If, in compound VII, $R_8$ is OH the acid may be esterified or formed into an amide using any known method in the art. For example, the methyl ester may be formed using diazomethane in an ether solution. Alternatively, the acid chloride can be formed using $SOCl_2$ or $POCl_3$ in an inert solvent and then the acid chloride treated with alcohol in the presence of a base such as pyridine. To form the amide, the acid chloride may be treated with two moles of a suitable amine.

(x) The hydroxy group on the tetrahydrofuran ring can be oxidised using an oxidising agent such as chromium trioxide in pyridine or any of the oxidising agents mentioned in paragraph (i) above.

A method of producing certain compounds of the general Formula I is illustrated by Scheme (b):

(i) Compound (1) in which Tr is a base stable blocking group such as triphenylmethyl or benzyl and $R_{10}$ and $R_{11}$ are as defined for formula I is converted to compound (2) by means of a modified Wittig reaction (Rosenthal A and Nguyen L, Benzing. J. Org. Chem. 34, 1029, 1969).

(ii) Compound (2) is reduced to compound (3) and then oxidised to compound (4). The reduction may be effected by means of lithium aluminium hydride in the presence of an anhydrous inert solvent and oxidation may be achieved by means of dimethylsulphoxide-dicyclohexylcarbodiimide in the presence of a catalyst such as pyridinium trifluoroacetate and by chromium trioxide in pyridine.

(iii) The first side chain is then added by means of a Wittig reaction to produce a compound (5). Y, $R_4$, $R_5$ and $R_8$ are as defined for formula I and the 5,6 double bond is cis.

(iv) The group Tr of compound (5) is removed and the resulting compound oxidised to produce a compound (7). The removal may be achieved by means of catalytic hydrogenation or, if the double bond is not to be reduced, by means of a mild acid. The oxidation may be achieved using the oxidising agents mentioned in paragraph (ii).

(v) The second side chain is added by means of a modified Wittig reaction as described in paragraph (ii) for Scheme (a) to produce compound (8). In compound (8), Z, D, $R_3$ and $R_2$ are as defined for compound IV. If D is =O, it may be reduced in the manner described above in paragraph (iii) for Scheme (a).

(vi) If the resulting product is a racemic mixture, resolution may be achieved using any of the methods known in the art as described above.

The above described methods, starting at any stage and proceeding to finality provides other aspects of the invention.

The invention is illustrated by the following examples:

EXAMPLE I (a)

(3R)-3-{Carboxymethyl-3,4-δ-lactone}-(4R)-4-hydroxy-(2S)-2-{3'-oxo-trans-1'-octenyl}tetrahydrofurane (IV')

A mixture of 1,4-anhydro-3-C-(carboxymethyl-2,3-δ-lactone)-3-deoxy-D-allitol (2,5 g) (Formula II) and sodium metaperiodate (2,84 g) in 50 ml. 80% ethanol was stirred at room temperature for 15 minutes.

After the addition of ether (50 ml) the mixture was filtered to remove the precipitated sodium iodate (NaIO₃). The filtrate was evaporated in vacuo, the residue taken up in 20 ml ethylacetate, dried over Na₂SO₄, filtered and the solvent removed under reduced pressure to give an oil. This was dissolved in 200 ml dry benzene and refluxed in a Dean-Stark apparatus for 45 minutes. Removal of the benzene under reduced pressure gave 1,77 g 1,4-anhydro-3-C-(carboxymethyl-2,3-γ-lactone)-3-deoxy-D-ribitol-5-aldehyde (Formula III) as an oil.

ν max CHCl₃ 1780 (C=O lactone) and 1740 (C=O aldehyde) cm⁻¹. The compound was not further characterised but immediately used for the next reaction.

To a suspension of sodium hydride (0,272 g 60% dispersion in oil) in 65 ml dry dimethoxyethane (DME) under N₂ at 0° C. was added a solution of 1,92 g dimethyl 2-oxoheptyl phosphonate in 10 ml dry DME. The mixture was stirred at room temperature for 30 min, cooled to 0° C., a solution of 1,06 g of compound of Formula III above in 25 ml dry DME was added and the mixture stirred for a further 2 hr at room temperature. After neutralisation with acetic acid the solution was filtered through celite and the filtrate evaporated to dryness under reduced pressure. The oil obtained was chromatographed on silicagel with ethyl acetate/n-hexane (1:4 → 2:3) to give 1,39 g of a compound

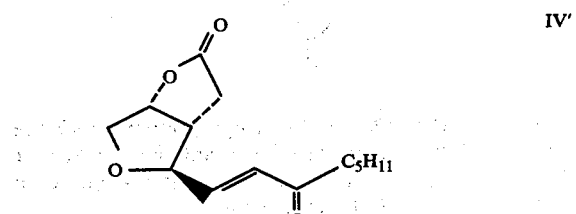

IV' which crystallized from ether-petroleum-ether (40°–60°) as plates mp 65°–67° C. $\{\alpha\}_D^{22}$ + 34° (c 0,9 CHCl₃)

I R Spectrum ν max CHCl₃ 1790 (C=O lactone) 1680 (C=O) and 1640 (CH=CH) cm⁻¹

Found: C 66,60; H 7,91 C₁₄H₂₀O₄ requires C 66,67 H 7,99

N.M.R. in CDCl₃:

δ0,87 (3H, t J=7,0 Hz, CH₂—<u>CH₃</u>)
δ1,2–1,74 (6H, m, —(CH₂)₃—)
δ2,54–3,02 (3H, m, H-3 and

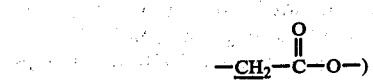

δ3,94–4,23 (2H, m, H-5(α+β))
δ4,32 (1H, t, H-2, $J_{2,3} = J_{2,1'} = 5$ Hz)
δ5,08 (1H, m, H-2)
δ2,52 (2H, t, J=7 Hz

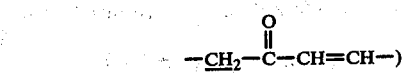

δ6,30 (1H, dd, H-2′, $J_{1',2'} = 15,75$ Hz, $J_{2,2'} = 1,0$ Hz)
δ6,66 (1H, dd, H-1′, $J_{1',2'} = 15,75$ Hz $J_{2,1'} = 5,0$ Hz)

(b)

(3R)-3-{Carboxymethyl-3,4-δ-lactone}-(4R)-4-hydroxy-(2S)-2-{(3'RS)-3'-hydroxy-trans-1'-octenyl}•tetrahydrofurane (IV″)

To sodium borohydride (1,95 g) in dry dimethoxyethane (50 ml) was added recently fused ZnCl₂ (3,4 g). The mixture was stirred for 18 hr at 0°–5° C. After filtration under nitrogen, the clear solution (ca 0,5 M) was used immediately.

To 252 mg IV′ dissolved in anhydrous DME (4 ml) was added 1,0 ml of the zinc borohydride solution. The mixture was stirred at room temperature until the reduction was complete (about 60 min) saturated potassium hydrogen tartrate was added dropwise until no further evolution of gas was observed. Ethyl acetate (25 ml) was then added, the solution was dried over sodium sulphate, filtered and the filtrate evaporated to dryness to give a colourless oil. This was purified on a silicagel column with chloroform and chloroform/methanol (95:5) to give an oil (245 mg) which crystallised upon standing. Recrystallisation from chloroform-petroleum ether (40°-60°) gave a compound

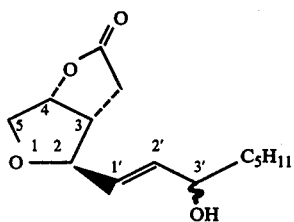

IV‴ as plates, mp 94°-97° C. $[\alpha]_D^{22} + 4°$ C. (C 1,8 CHCl$_3$) $\nu$ max CHCl$_3$ 3480 (OH) 1780 (C=O), 1610 (CH=CH) cm$^{-1}$ N.M.R. in CDCl$_3$:
δ0,90 (3H, t, J=6,0 Hz, —CH$_2$—C$\underline{H}_3$)
δ1,20-1,60 (8H, m, —(CH$_2$)$_4$—)
δ2,35-2,98 (3H, m, H-3 and

δ3,88-4,27 (4H, m,

H-5($\alpha+\beta$) and H-2
δ5,08 (1H, m, H-4)
5,74 (2H, m, —CH=CH—)

(c)
(3R)-3-{Carboxymethyl-3,4-γ-lactone}-(4R)-4-hydroxy(2S)-2-{(3'RS)-3'-tetrahydropyranyloxy-trans-1'-octenyl}tetrahydrofurane V'.

To a solution of 1,02 g (4,017 mmoles) IV‴ in anhydrous dichloromethane (10 ml) was added a solution of 1,5 ml toluenesulphonic acid monohydrate (TsOH) in THF (50 mg TsOH/10 ml THF) and 0,66 ml dihydropyrane. The mixture was stirred at room temperature for 30 min. and the reaction was followed by thin layer chromotography (tlc). Pyridine (15 drops) was added and then dichloromethane (40 ml). The solution was washed with a saturated sodium chloride solution, dried over Na$_2$SO$_4$ and filtered. Evaporation of the solvent under reduced pressure gave an oil which was purified on a silicagel column with CHCl$_3$ → 5% MeOH/CHCl$_3$ to yield 1,31 g of a compound V as an oil with the OH blocked as the tetrahydropyranyl ether.

$\nu$ max CHCl$_3$ 1780 (C=O) cm$^{-1}$ and no —OH absorption.

(d)
(3R)-3-{Formylmethyl-3,4-γ-lactol}-(4R)-4-hydroxy-(2S)-2-{(3'RS)-3'-tetrahydropyranyloxy-trans-1'-octenyl} tetrahydrofurane (VI')

A solution of 1,20 g of V' in anhydrous toluene (10 ml) under nitrogen was cooled to −60° C. A solution of 5,8 ml diisobutylaluminiumhydride (20% soln. in hexane) was added dropwise. The mixture was stirred for 20 minutes at −60° C. Excess reagent was destroyed by the dropwise addition of methanol until the evolution of gas ceased. Stirring was continued for an additional 15 minutes at room temperature. Ethyl acetate (50 ml) was added, the solution was dried over sodium sulphate and filtered. Evaporation of the solvent under reduced pressure and purification of the residue on a silicagel column with chloroform → 5% methanol/chloroform gave 1,15 g of oily lactol:

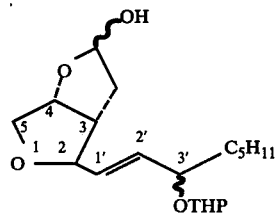

VI'

$\nu$ max CHCl$_3$ 3420 (—OH) and 1610 (CH=CH) cm$^{-1}$.

(e)
{8R,12S}-(9R,15S)-9,15-Dihydroxy-11-oxa-prosta-cis-5:6-trans-13:14-dienoic acid (VIII).

A mixture of 0,96 g (24 mmole) of 60% sodium hydride in mineral oil and 10 ml dimethylsulfoxide (DMSO) was stirred under N$_2$ at 70°-75° C. for 45 minutes. The resulting dark solution was cooled to 5° C. To this was added a solution of 5,88 g (12 mmoles) of 4-carboxybutyl-triphenylphosphonium iodide in 10 ml DMSO. The resulting dark-red solution was stirred for 30 minutes at ambient temperature and cooled to 5° C. To this solution was added 1,36 g (4 mmoles) of the lactol produced in the previous step dissolved in 2 ml DMSO. The resulting mixture was allowed to stir for 15 hr. at room temperature. The mixture was added to ice and water (200 ml) and the solution extracted with petroleum ether (40°-60° C.) and ether to remove neutral impurities. The aqueous phase was acidified with oxalic acid to pH2 and extracted with ether (3×50 ml). The organic layer was washed with a saturated sodium chloride solution dried over sodium sulphate and filtered. Evaporation of the solvent in vacuo gave crude product as an oil which was immediately hydrolysed by stirring a solution of it in 10 ml acetic acid/water (7:3) for 4 hr. at ambient temperature. Evaporation of the solvent under reduced pressure below 50° C. yielded an oil (1,82 g). This was chromatographed on preparative tlc plates with glacial acetic acid/ethyl acetate (2:98) to give 500 mg of compound VIII as an oil and 300 mg of the slightly more polar compound VIIIa as an oil which crystallised upon standing. Compound VIIIa was recrystallized from ether-petroleum ether (bp 40°-60°) at 4° C.

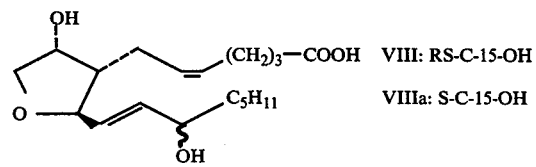

VIII: RS-C-15-OH
VIIIa: S-C-15-OH (VIII)

Compound VIIIa Found C 67,0; H 9,4. C$_{19}$H$_{32}$O$_5$ requires C 67,0 H 9,7.

mp 66°-67° C. $\{\alpha\}_D^{26}$ + 59° (c 1,3 —CHCl$_3$)

ν max CHCl$_3$ 3450 (OH) 1720 (C=O) and 1610 (CH=CH) cm$^{-1}$

N.M.R. in CDCl$_3$

δ0,89 (3H, t, J=6,0 Hz, CH$_2$—CH$_3$)

δ1,20-2,26 (15H, m, H-8 and CH$_2$ of aliphatic chains)

δ2,33 (2 H, t, J=7,0 Hz —CH$_2$—CO$_2$H)

δ3,77-4,22 (4H, m, H-9, H-10 (α + β) and H-15)

δ4,31 (1H, t, H-12, J$_{8,9}$ = J$_{12,3}$ = 4,0Hz)

δ5,43 (2H, m, H-5 and H-6)

δ5,68 (2H, m, H-13 and H-14)

δ5,20 (3H, (broad) OH and CO$_2$H disappears upon addition of D$_2$O)

Enantiomeric mixture VIII

Analysis Found: C 66,9 H 9,5. C$_{19}$H$_{32}$O$_5$ requires C 67,0 H 9,7.

$\{\alpha\}_D^{26}$ + 42° (c 1,4 CHCl$_3$)

ν max CHCl$_3$ 3460 (OH), 1720 (C=O) and 1610 (CH=CH) cm$^{-1}$

N.M.R. in CDCl$_3$

δ0,89 (3H, t, J=6,0 Hz, —CH$_2$—CH$_3$)

δ1,20-2,26 (15H, H-8 and CH$_2$ of aliphatic chains)

δ2,34 (2H, t, J=7,0 Hz, —CH$_2$—CO$_2$H)

δ3,60-4,40 (5H, m, H-9, H-10 (α + β), H-12 and H-15)

δ5,20 (broad singlet 3H, OH and CO$_2$H disappears upon adn of D$_2$O)

δ5,46 (2H, m, H-5 and H-6).

δ5,69 (2H, m, H-13 and H-14).

(f) A solution of compound VIII (2,88 g) in ether (25 ml) was treated with a solution of diazomethane in ether until the yellow colour of the reaction mixture persisted. The mixture was left at room temperature for 15 minutes. Evaporation of the solvent in vacuo gave an oil (3,0 g). The mixture of C - 15 epimers was separated by column chromatography on silica gel using ethylacetate-benzene (2,5:7,5)→(1:1) to give compound VIIIb (1,6g) as an oil and compound VIII c (1,29g) which was crystallised from ether-petroleum ether (40°-60°).

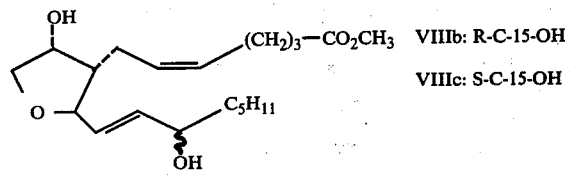

VIIIb: R-C-15-OH
VIIIc: S-C-15-OH compound VIIIb: Found: C 67,7; H 9,6 C$_{20}$H$_{34}$O$_5$ requires: C 67,8; H 9,7

$[\alpha]_D^{22}$ + 40° (c 4,8 CHCl$_3$).

ν max (CHCl$_3$) 3450 (OH) 1730 (ester) cm$^{-1}$

N.M.R. in CDCl$_3$

δ0,87 (3H, t, J=6,0Hz, CH$_2$—CH$_3$)

δ1,20-2,20 (1H, m, H-8 and CH$_2$ of aliphatic chains)

δ2,32 (2H, t, J=7,0Hz, —CH$_2$—CO$_2$CH$_3$)

δ3,54-4,16 (4H, m, H-9, H-10 (α + β) and H-15)

δ3,64 (3H, s, CO$_2$CH$_3$)

δ4,50 (1H, t, H-12 J$_{8,9}$ = J$_{12,13}$ = 4,0Hz)

δ5,40 (2H, m, H-5 and H-6)

δ5,68 (2H, m, H-13 and H-14)

δ2,30 (2H, OH exchangeable with D$_2$O)

Compound VIIIc Found C 67,7; H 9,8 C$_{20}$H$_{34}$O$_5$ requires: C 67,8; H 9,7 mp 64°-65° C. $[\alpha]_D^{22}$ + 51° (c 3,4 CHCl$_3$)

ν max (CHCl$_3$ 3450 (OH) and 1730 (ester) cm$^{-1}$

N.M.R. in CDCl$_3$

δ0,87 (3H, t, J = 6,0Hz, CH$_2$—CH$_3$)

δ3,65 (3H, s, CO$_2$CH$_3$)

δ4,50 (1H, t, H-12, J$_{8,9}$ = J$_{12,13}$ = 3,8Hz)

δ5,40 (2H, m, H-5 and H-6)

δ5,66 (2H, m, H-13 and H-14)

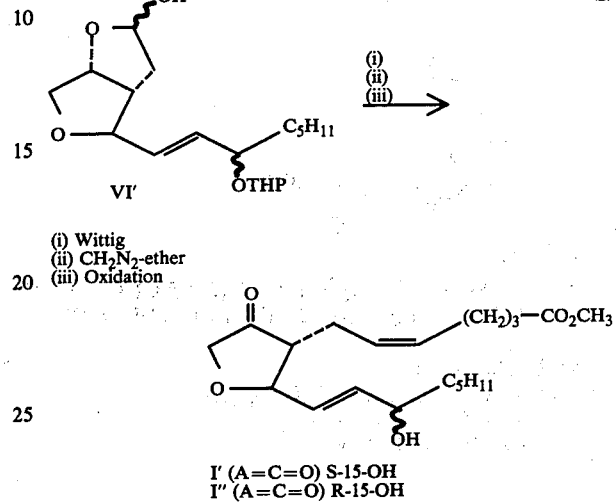

(i) Wittig
(ii) CH$_2$N$_2$-ether
(iii) Oxidation

I' (A=C=O) S-15-OH
I" (A=C=O) R-15-OH

A mixture of 600 mg (ca. 20 mmoles) of 80% sodium hydride in mineral oil in 15 ml anhydrous DMSO was stirred under nitrogen at 70°-75° C. for 1,5 hours. The resulting solution was cooled to 5° C. To this was added 4,41 g (9,8 mmoles) of 4-carboxybutyl-triphenylphosphonium iodide. The resulting red solution was stirred 1 hr at ambient temperatures. To this solution was added 1 g (2,94 mmoles) of compound VI' in anhydrous DMSO (5 ml). The resulting mixture was allowed to stir for 16 hours at ambient temperature, and then added to 250 ml ice-water saturated with sodium chloride. Extraction with ether (3 × 50 ml) removed triphenylphosphine oxide and neutral impurities. Acidification of the aqueous phase with oxalic acid to pH ≦ 1 and extraction with ether (3 × 50 ml) gave after drying and evaporation of the solvent 1g of an oil. Chromatography on silica gel with 5 → 10% methanol-chloroform gave 650 mg of 9α-hydroxy-11-oxa-15-tetrahydropyranyloxy-prosta-cis-5:6-trans-13:14-dienoic acid. This compound was dissolved in ether (10 ml) and treated with a solution of diazomethane in ether until the yellow colour persisted. Evaporation of the solvent in vacuo gave an oil (672 mg). This compound was added to a solution of 900 mg of chromium trioxide and 1,42 g of pyridine in 30 ml anhydrous dichloromethane and the resulting mixture was stirred for 15 minutes at room temperature. The solution was filtered and the precipitate was washed with 150 ml dichloromethane. The filtrate was extracted with 30 ml of a 5% sodium hydroxide, 30 ml 5% aqueous HCl and 30 ml 5% aqueous NaHCO$_3$. After drying over Na$_2$SO$_4$ the organic phase was evaporated under reduced pressure to yield an oil (500 mg). This was stirred with 10 ml of a mixture of acetic acid-water (7:3). Evaporation of the solvent in vacuo and chromatography of the residual oil on silica gel with ethyl acetate-benzene (2,5:7,5) gave 220 mg of compound I' as an oil and 160 mg of compound I" as an oil.

Compound I' Found: C 68,0; H 9,3. C$_{20}$H$_{32}$O$_5$ requires C 68,2; H 9,2.

$[\alpha]_D^{22}$ − 37° (c 2,1 CHCl$_3$)

ν max 3480 (OH), 1725 (C=O) and 1750 (ester) cm$^{-1}$

N.M.R. in CDCl$_3$

δ0,87 (3H, t, J=6,0Hz, CH$_2$—CH$_3$)
δ1,20-2,40 (17H, m, H-8 and CH$_2$ of aliphatic chains)
δ2,02 (1H, s, OH, exchangeable with D$_2$O)
δ3,65 (3H, s, CO$_2$CH$_3$)
δ3,80-4,40 (4H, m, H-10 (α + β), H-12 and H-15)
δ5,40 (2H, m, H-5 and H-6)
δ5,82 (2H, m, H-13 and H-14)

Compound I" Found: C 68,1; H 9,1. C$_{20}$H$_{32}$O$_5$ requires C 68,2; H 9,2.

$[α]_D^{22}$ − 52° (c 3,2 CHCl$_3$)

ν max 3480 (OH), 1725 (C=O) and 1750 (ester) cm$^{-1}$

N.M.R. in CDCl$_3$

δ0,90 (3H, t, J=6,0Hz, CH$_2$—CH$_3$)
δ1,20-2,0 (17H, m, H-8 and CH$_2$ of aliphatic chains)
δ3,65 (3H, s, CO$_2$CH$_3$)
δ3,80-4,4(4H, m, H-10 (α+β), H-12 and H-15)
δ5,40 (2H, m, H-5 and H-6)
δ5,81 (2H, m, H-13 and H-14)
δ2,0 (1H, s, OH, exchangeable with D$_2$O)

The above methods are examples of the method of Scheme (a).

EXAMPLE II

This method is an example of the method represented diagrammatically by Scheme (b). The numbers identify the various compounds in relation to the compounds of Scheme (b).

3-C-Carbomethoxymethyl-3-deoxy-1,2-O-isopropylidene-5-O-trityl-α-D-ribofuranose (2)

An ice-cold solution of phosphonoacetic acid trimethyl ester (22 ml) and anhydrous potassium t-butoxide (5 g) in anhydrous N,N-dimethylformamide (DMF) (20 ml) was slowly added to a solution (kept at 0° C.) of 18,32 g of 1,2-O-isopropylidene-5-O-trityl-α-D-erythro-pentofuranos-3-ulose* (1) in 50 ml anhydrous N,N-dimethylformamide. The mixture was stirred under dry nitrogen at 0° C. for 1 hr and then at room temperature for 48 hrs. The solvent was removed under reduced pressure and the residue, after addition of 250 ml water, was extracted twice with ether (200 ml), the ether layer was washed with water (50 ml), dried over sodium sulphate and filtered, and the filtrate evaporated under reduced pressure. The residue was purified on a silica gel column with ethyl acetate-cyclohexane (1:4) : yield 19,75g of syrup. This was reduced in 100 ml absolute ethanol under 2 atm hydrogen pressure with ca 6 g Raney nickel for 1,5 hr. at room temperature. The mixture was filtered. Evaporation of the filtrate yielded 19,3 g (92%) of compound (2) which crystallised from ether - petroleum ether (40°-60°) as needles: mp 114°-115°, $[α]_D^{23}$ + 34° (C 1,2 CHCl$_3$) ν max (CHCl$_3$) 1745 (ester) cm$^{-1}$, M+ 488

* (see W. Sowa, Can. J. Chem., 46, 1586 (1968))

Analysis Found: C 73,6 H 6,6. C$_{30}$H$_{32}$O$_6$ requires C 73,7 H 6,6.

3-Deoxy-3-C-(2'-hydroxyethyl)-1,2-O-isopropylidene-5-O-trityl-α-D-ribofuranose (3)

To a stirred solution of 19,2 g of the branch-chain sugar (2) in 150 ml anhydrous tetrahydrofurane was added, portionwise, 2 g of lithium aluminium hydride. The mixture was stirred for 1,5 hr. at room temperature, cooled in an ice-bath and the excess of lithium aluminium hydride decomposed by the dropwise addition of water. The mixture was filtered, the residue washed with tetrahydrofurane, and the filtrate evaporated under reduced pressure: yield 18 g syrup. Chromatography of the latter on silica gel with chloroform gave 17 g (84%) of chromatographically homogeneous (3) as a syrup, $[α]_D^{23}$ + 36° (C 1,8 CHCl$_3$), δ7,2 to 7,5 (15H, m, C(C$_6$H$_5$)$_3$), δ5,88 (1H, doublet, H-1, J$_{1,2}$ = 4Hz), δ4,68 (1H, triplet, H-2, J$_{2,3}$ = 4Hz), δ3,94 (1H, multiplet, H-4), δ3,6 (2H, triplet, H-2', J$_{1',2'}$ = 7 Hz), δ3,04 to 3,54 (2H, multiplet, H-5 and H-5'), δ2,2 (1H, multiplet, H-3); δ1,5-1,96 (2H, multiplet, H-1'), δ1,86 (1H, singlet, OH exchangeable with D$_2$O) δ1,33 and 1,5 (6H, two singlets, (CH$_3$)$_2$C), M+ 460

Analysis Found: C 75,6 H 7,0. C$_{29}$H$_{32}$O$_5$ requires C 75,6 H 7,0.

3-Deoxy-3-C-formylmethyl-1,2-O-isopropylidene-5-O-trityl-α-D-ribofuranose (4)

To a stirred solution of 2,85 g pyridine in 50 ml methylene chloride under nitrogen was added 1,8 g of chromium trioxide with cooling. This mixture was stirred an additional 15 min. at room temperature. A solution of 1,4 g of compound (3) in 10 ml methylene chloride was added rapidly to the Collins oxidant solution and stirred at room temperature for 20 min. The methylene chloride was decanted and the black precipitate washed twice with methylene chloride (150 ml). The solution was washed with a solution of 5% sodium hydroxide, 5% hydrochloric acid and 5% sodium hydrogencarbonate, dried over sodium sulphate filtered and evaporated: yield 1,3 g crude (4) which was chromatographed on silica gel with ethyl acetate-cyclohexane (1:4) to give 1,15 g (82%) of compound (4). The compound was dried by refluxing with a 100 ml anhydrous benzene in a Dean-Stark apparatus and crystallised from ether, mp. 136°-138° (plates), $[α]_D^{23}$ + 49° (c 1,2 CHCl$_3$), ν max (CHCl$_3$) 2800, 2700 and 1720 (CHO) cm$^{-1}$, NMR in CDCl$_3$ δ9,66 (1H, singlet, CHO), δ7,2 to 7,5 (15H, (C$_6$H$_5$)$_3$C), δ5,87 (1H, doublet, H-1, J$_{1,2}$ = 4Hz) δ4,78 (1H, triplet, H-2, J$_{2,3}$ = 4Hz), δ3,91 (1H, m, H-4), δ3,12 to 3,46 (2H, m, H-5 and H-5'), δ2,1 to 2,9 (3H, m, H-1' and H-3), δ1,3 and 1,47 (6H, two singlets, (CH$_3$)$_2$C)

Analysis Found: C 75,9 H 6,6 C$_{29}$H$_{30}$O$_5$ requires C 76,0 H 6,6

3-C-(6'-Carboxy-cis-2'-hexenyl)-3-deoxy-1,2-O-isopropylidene-5-O-trityl-α-D-ribofuranose (5)

A mixture of 276 mg of 50% sodium hydride in mineral oil and 10 ml anhydrous dimethyl sulfoxide was stirred under nitrogen at 70°-75° for 45 min. The resulting dark solution was cooled to 5°. To this was added a solution of 1,47 g of 4-carboxybutylphosphonium iodide in 5 ml anhydrous dimethyl sulfoxide. The resulting dark-red solution was stirred at room temperature for 10 min. and then added to a solution of compound (4) in 2 ml anhydrous dimethyl sulfoxide kept at 5° under nitrogen. The mixture was allowed to stir for 3 hr at room temperature. The mixture was added to ice and water (100 ml) and the solution acidified with 5% hydrochloric acid and extracted twice with benzene (150 ml). The benzene extract was washed with water (50 ml), dried over sodium sulphate, filtered and the filtrate evaporated under reduced pressure. The residue was chromatographed on silica gel with benzene and 10 to 50% ethyl acetate-benzene mixtures:yield 449 mg of compound (5) which crystallised from ether as plates, mp 164,5°-165,5°, $[\alpha]_D^{23} + 48°$ (c 1,3 CHCl$_3$); $\nu$ max (CHCl$_3$); 1705 (C=O) cm$^{-1}$ NMR in CDCl$_3$ $\delta$7,1 to 7,6 [15H, multiplet, (C$_6$H$_5$)$_3$C], $\delta$5,88 (1H, doublet, H-1, J$_{1,2}$ = 4Hz), $\delta$5,33 (2H, multiplet, CH=CH), $\delta$4,51 (1H, triplet, H-2, J$_{2,3}$ = 4Hz), $\delta$3,94 (1H, multiplet, H-4), $\delta$3,02 to 3,54 (2H, m, H-5) H $\delta$2,25 (2H, triplet, J=7Hz, CH$_2$—CH$_2$—CO$_2$H), $\delta$1,52 and 1,34 [6H, two singlets, (CH$_3$)$_2$C]

Analysis Found: C 75,1 H 7,0. C$_{34}$H$_{38}$O$_6$ requires C 75,3 H 7,1.

3-C-(6'-carboxyhexyl)-3-deoxy-1,2-O-isopropylidene-α-D-ribofuranose (6)

A mixture of 7 g of compound (5) and platinum oxide (1 g) in 100 ml of glacial acetic acid was shaken in a Parr apparatus for 19 hr under two atmospheres of hydrogen pressure. The mixture was filtered and the filtrate evaporated in vacuo at a temperature below 40°. The residue was chromatographed on silica gel with ethyl acetate-benzene (1:9) and ethyl acetate to give 3,6 g (93%) of compound (6), which crystallised from ether as plates, mp 99°-100°, [α] + 63° (C 1,2 CHCl$_3$) $\nu$ max (CHCl$_3$) 3500 (OH) and 1715 (C=O) cm$^{-1}$.

Analysis Found: C 59,8 H 8,6. C$_{15}$H$_{26}$O$_6$ requires C 59,6 H 8,7.

3-C-(6'-Carbomethoxyhexyl)-3-deoxy-1,2-O-isopropylidene-α-D-ribofuranose (6',R=OCH$_3$)

A solution of 2,7 g of compound (6) in 5 ml of absolute ethanol and 15 ml ether was treated with a saturated solution of diazomethane in ether until the yellow colour persisted and then left at ambient temperature for 10 min. The solvent was removed in vacuo to give 2,8 g of (7) as a syrup, $[\alpha]_D^{22} + 57°$ (C 2,3 CHCl$_3$), $\nu$ max (CHCl$_3$) 3500 (OH) and 1750 (ester) cm$^{-1}$. NMR in CDCl$_3$ $\delta$5,8 (1H, doublet, H-1, J$_{1,2}$ = 4 Hz), $\delta$4,65 (1H, triplet, H-2, J$_{2,3}$ 4Hz), $\delta$3,4 to 3,92 (3H, H$_4$ and H-5), $\delta$3,68 (3H, singlet, OCH$_3$), $\delta$2,75 (1H, triplet, J=6Hz, OH exchangeable with D$_2$O), $\delta$2,34 (2H, triplet, J=7Hz, CH$_2$ — CO$_2$CH$_3$).

Analysis Found: C 60,6 H 9,0. C$_{16}$H$_{28}$O$_6$ requires C 60,7 H 8,9.

Oxidation of Compound (6') to give the Aldehyde (7) and Wittig reaction to 3-C-(6'-carbomethoxyhexyl)-3,5-dideoxy-1,2-O-isopropylidene-5-(2'-oxo-heptylidene)-α-D-ribofuranose (8): Compound (6') (2,1 g) was dissolved in anhydrous dimethyl sulfoxide (9 ml) and benzene (9 ml) containing pyridine (0,52 ml) at trifluoroacetic acid (0,26 ml). After addition of dicyclohexylcarbodiimide (4,1 g) the sealed reaction was kept at room temperature for 20 hr. Ether (100 ml) was added followed by a solution of oxalic acid dihydrate (2,52 g) in 10 ml methanol. After gas evolution had ceased (ca 30 min.) water (100 ml) was added and the insoluble dicyclohexylurea removed by filtration. The water layer was extracted with a further 100 ml of ether and the combined ether extracts washed twice with a 5% sodium bicarbonate solution, once with water and dried over sodium sulphate and filtered. The solvent was removed under reduced pressure, and the residue chromatographed on silica gel with 10 to 20% ethyl acetate-benzene to give an oil which was refluxed with 100 ml anhydrous benzene for 45 minutes in a Dean-Stark apparatus. Removal of the solvent in vacuo afforded 1,5 g (7) as an oil. This compound did not show any absorption at ca 3500 cm$^{-1}$ in the ir spectrum and strong absorption at 1745 cm$^{-1}$ and was immediately used for the next reaction without further characterisation.

To a suspension of 149 mg sodium hydride (50% dispersion in mineral oil) in 30 ml anhydrous tetrahydrofurane, under nitrogen at 0° C., was added a solution of 690 mg dimethyl (2-oxoheptyl) phosphonate in 5 ml anhydrous tetrahydrofurane and the mixture stirred at ambient temperature for 30 min. The mixture was again cooled to 0° C. and a solution of 871 mg of compound (7) in 5 ml anhydrous tetrahydrofurane slowly added. Stirring was continued for 2 hrs. at room temperature. The solution was neutralised with acetic acid and filtered through celite. Evaporation of the solvent under reduced pressure gave an oil which was purified on silica gel with ethyl acetate benzene (5:95) to yield 911 mg of compound (8) as an oil. $\{\alpha\}_D^{23} + 32°$ (C 0,9 CHCl$_3$), $\nu$ max (CHCl$_3$) 1730 (ester) 1690 (C=O) and 1640 (C=C) cm$^{-1}$.

Analysis Found: C 67,2 H 9,2. C$_{23}$H$_{38}$O$_6$ requires C 67,4 H 9,3.

Zinc borohydride reduction of compound (8) to give Methyl {8R,12S}-11-oxa-9,10-isopropylidene-(9R,10R,15RS)-9,10,15-trihydroxy-prost-trans-13:14-enoate (8'))

To a solution of compound (8) (1,1 g) in 5 ml anhydrous dimethoxyethane was added a solution (ca 0,5 M) of 2,7 ml of zinc borohydride in dimethoxyethane. The mixture was stirred for 1,5 hr at ambient temperature. A saturated, aqueous solution of potassium hydrogen tartrate was added dropwise to the reaction mixture until no further evolution of gas was observed. Chloroform (30 ml) was then added, the solution dried over sodium sulphate, filtered and evaporated under reduced pressure to give an oil. This was purified on a silica gel column with ethanol-chloroform (1:99) to give 0,94 g of the epimeric mixture of alcohols (8') as an oil, $\{\alpha\}_D^{23} + 31°$ (c 5,6 CHCl$_3$), $\nu$ max (CHCl$_3$), 3,610, 3440 (OH), 1740 (ester) cm$^{-1}$ NMR in CDCl$_3$:

$\delta$5,78 (1H, doublet, H-10, J$_{9,10}$ = 3,8 Hz), $\delta$4,6 (1H, triplet, H-9, J$_{8,9}$ = 4Hz), $\delta$5,42 to 5,92 (2H, m, H-13 and H-14), $\delta$4,0 to 4,22 (2H, m, H-12 and H-15), $\delta$3,66 (3H, singlet CO$_2$ CH$_3$), $\delta$2,31 (2H, triplet, J = 7Hz, CH$_2$—CO$_2$CH$_3$), $\delta$2,09 (1H, broad singlet, OH exchangeable with D$_2$O), $\delta$1,52 and 1,33 {6H, two singlets, (CH$_3$)$_2$ C}.

Analysis Found: C 66,7 H 9,7. C$_{23}$H$_{40}$O$_6$ requires C 67,0 H 9,8.

Chromatography of the epimeric mixture of alcohols (8') (800 mg) on silica gel with ethyl acetate-benzene (2,5:7,5) eluant gave the 15-S-compound(8'') (380 mg) and the 15 R-isomer (8''') (370 mg) as oils.

Compound (8'') Found: C 66,9; H 9,7 C$_{23}$H$_{40}$O$_6$ requires C 67,0; H 9,8

$[\alpha]_D^{22} + 35°$ (c, 1,5 CHCl$_3$)

Compound (8''') Found: C 66,8; H 9,8 C$_{23}$H$_{40}$O$_6$ requires C 67,0; H 9,8

$[\alpha]_D^{22} + 26°$ (c, 2,4 CHCl$_3$)

We claim:

1. A compound of the following formula:

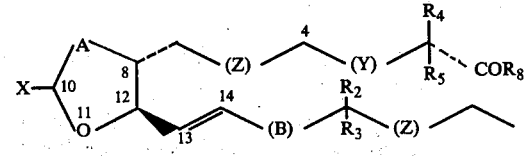

wherein

A represents —C=O or α—C . . . OH

B represents

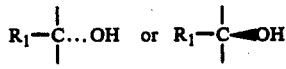

$R_1$ represents H, lower alkyl or halogen substituted lower alkyl

Z represents $CH_2$—$CH_2$ or C≡C in the cis configuration $R_2$ and $R_3$, the same or different, represent H or halogen substituted or unsubstituted lower alkyl;

Y is —S—, —O— or —$CR_6R_7$ $R_4$, $R_5$, $R_6$ and $R^7$, the same or different, represent H, halogen substituted or unsubstituted lower alkyl or halogen X is H or OH $R_8$ is $OR_9$ or $NR_9R_9$ $R_9$ is H or lower alkyl group, and when X is OH and A is α—C...OH then together they may form the group

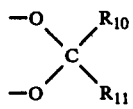

wherein $R_{10}$ and $R_{11}$, the same or different, are lower alkyl, hydrogen or a carbocyclic group of 4 to 6 carbon atoms.

2. A compound of claim 1 wherein B is

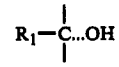

$R_1$ is H or methyl;

$R_2$ and $R_3$, the same or different, are H or methyl;

$R_4$, $R_5$, $R_6$ and $R_7$, the same or different are H, lower alkyl or fluoro;

$R_9$ is H or lower alkyl; and

A, Y, X and $R_8$ are as defined in claim 1.

3. A compound of claim 1 substantially free of other geometric and optically active isomers.

4. A compound of claim 2 substantially free of other geometric and optically active isomers.

5. 9α,15α-dihydroxy-11-oxa-prosta-cis-5:6-trans-13:14 dienoic acid.

6. The compound of claim 5 substantially free of other geometric and optically active isomers.

7. 15α-hydroxy-11-oxa-9-oxo-prosta-cis-5:6-trans-13:14-dienoic acid methyl ester.

8. The compound of claim 7 substantially free of other geometric and optically active isomers.

9. 9α,10α,15α-trihydroxy-11-oxa-9:10-isopropylidene-prost-trans-13:14-enoic acid methyl ester.

10. The compound of claim 9 substantially free of other geometric and optically active isomers.

* * * * *

Disclaimer 4,133,817.—*Gerhardus J. Lourens*, Rand Park Ridge Extn 1 and *Johannes M. Koekemoer*, Pretoria, both of South Africa. 11-OXA-PROSTAGLANDIN ANALOGS. Patent dated Jan. 9, 1979. Disclaimer filed July 23, 1984, by the assignee, *Hoffmann-La Roche, Inc.*

Hereby enters this disclaimer to claims 1 and 2 of said patent.

[*Official Gazette October 23, 1984.*]